United States Patent [19]

Cimino

[11] Patent Number: 5,628,743

[45] Date of Patent: May 13, 1997

[54] DUAL MODE ULTRASONIC SURGICAL APPARATUS

[75] Inventor: William W. Cimino, Louisville, Colo.

[73] Assignee: Valleylab Inc., Boulder, Colo.

[21] Appl. No.: 360,538

[22] Filed: Dec. 21, 1994

[51] Int. Cl.$^6$ .................................................. A61B 17/36
[52] U.S. Cl. ............................ 606/1; 606/41; 606/169; 604/22
[58] Field of Search .......................... 606/1, 32, 37–42, 606/45, 169; 604/22

[56] References Cited

U.S. PATENT DOCUMENTS

| | | | |
|---|---|---|---|
| 4,634,420 | 1/1987 | Spinosa et al. | 604/22 |
| 4,886,060 | 12/1989 | Wiksell | 604/22 |
| 5,026,387 | 6/1991 | Thomas | 606/169 |
| 5,213,569 | 5/1993 | Davis | 604/22 |
| 5,263,957 | 11/1993 | Davison | 606/169 |
| 5,312,329 | 5/1994 | Beaty et al. | 604/22 |
| 5,451,220 | 9/1995 | Ciervo | 606/1 |

FOREIGN PATENT DOCUMENTS

WO9314709  8/1993  WIPO .

Primary Examiner—Angela D. Sykes
Assistant Examiner—Michael Peffley
Attorney, Agent, or Firm—Peter C. Richardson; Lawrence Akers; Aaron Passman

[57] ABSTRACT

A single ultrasonic surgical apparatus can provide a substantial cutting effect on tissue, a substantial coagulation effect on tissue, and an appropriate blend of simultaneous cutting and coagulation effects on tissue. The ultrasonic surgical apparatus is comprised of a handpiece which incorporates a transducer and a surgical tool, a source of electrical energy, a controller, and a switch. The apparatus may be operated at two frequencies within the ultrasonic spectrum, where the first frequency is selected at the low end of the spectrum for enhanced tissue cutting performance, and the second frequency is approximately three times higher for enhanced tissue coagulation performance. The two frequencies may be operated selectively or concurrently, and may be independently adjustable as to amplitude. The transducer may be composed of magnetostrictive or piezoelectric elements. The surgeon to set the desired amplitude of the mechanical vibrations. The transducer is mounted within the handpiece at a location that corresponds to a vibration node common to both the first frequency and the second frequency. Also claimed is a method for use, including the steps of: developing an ultrasonic resonance at a first frequency; developing an ultrasonic resonance at a second frequency which is approximately three times greater than the first frequency; resonating an ultrasonic transducer at the first frequency concurrently with the second frequency; and supporting the transducer where the nodes of vibration at the first frequency are substantially coincident with the nodes of vibration at the second frequency.

9 Claims, 2 Drawing Sheets

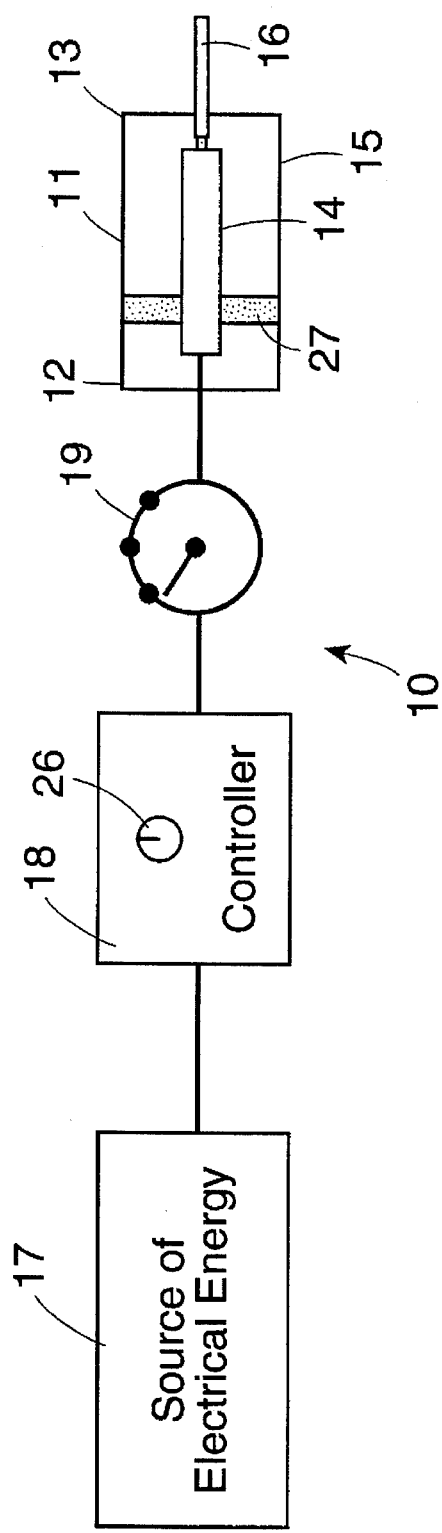
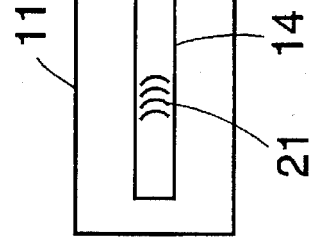
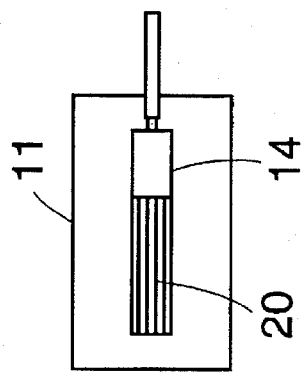
FIG. 1
FIG. 3
FIG. 2

DUAL MODE ULTRASONIC SURGICAL APPARATUS

FIELD OF THE INVENTION

This invention relates to an improved ultrasonic surgical apparatus for cutting and coagulating tissue of a patient, and more particularly to an ultrasonic surgical apparatus that has the capability of selective and/or concurrent delivery of ultrasonic energy at two different frequencies.

BACKGROUND OF THE DISCLOSURE

Current non-powered tools for tissue dissection such as the scalpel and associated instruments tend to cause bleeding at the incised area. There is nothing inherent in the tool which achieves hemostasis. Electrocautery, or more broadly, radio frequency electromagnetic energy based tools, can achieve hemostasis through the deposition of electrical currents in the tissue which effectively cauterize the bleeding tissue through resistive heating. The disadvantage of the electrocautery tools is that they do not make good fine-dissection tools, since the energy deposition is not precisely controlled, and the tool tips can stick to the tissue.

The use of ultrasonic energy in surgical procedures is known to those skilled in the art to be a valuable resource for cutting and fragmenting tissue of a patient. Most of these apparatus incorporate a sinusoidal driving signal which causes the mechanical tip to vibrate at a selected frequency, usually in the range of 20 kHz. to 60 kHz. The sinusoidal drive signal may be derived from a square wave at the same frequency or it may be inherent in the design. Further, some devices utilize duty-cycle modulated waveforms to achieve a desired effect.

It is also known to those skilled in the art that at the lower end of the preferred frequency spectrum, i.e. 20 kHz. to 40 kHz., larger tip displacements are possible. It is also known that larger tip displacements provide a better tissue cutting effect than small tip displacements.

Ultrasonic energy at the high end of the preferred frequency spectrum, i.e. 40 kHz. to 60 kHz., can have more hemostatic effect. This is due to the increased absorbance of higher frequency energy by tissue. However, larger tip displacements are not feasible at these frequencies. Therefore, devices which operate in this realm have reduced tissue cutting performance.

Several ultrasonic surgical devices have been disclosed which attempt to provide both tissue cutting and coagulation functions, U.S. Pat. No. 5,026,387 assigned to Ultracision, Inc., has several operating modes. Power is transmitted at an ultrasonic frequency to the instrument at a relatively high level when a surgical function is to be effected and the load on the instrument is relatively high. Power is transmitted to the instrument at a relatively low level during idle periods of use. A high power coagulation mode is manually selectable with automatic return to an idle power level when the blade is not in contact with tissue. There is no claim to operating at different frequencies.

In U.S. Pat. No. 5,263,957 assigned to Ultracision, Inc., the shape of an ultrasonic blade is disposed to provide a cutting function and a coagulation function. One portion of the blade is disposed to cut tissue. A second portion of the blade is disposed to provide frictional coupling of the blade edge and tissue to obtain tissue motion with resulting generation of heat and a hemostatic effect.

Foreign Patent WO 9,314,709 discloses an ultrasonic blade with a hook formed in the blade having flat, non-sharpened, relatively dull edges. This facilitates the cutting and coagulation of the tissue upon application of the ultrasonic energy to the tissue.

SUMMARY OF THE INVENTION

It is the general object of this invention to provide a single ultrasonic surgical apparatus that can provide a substantial cutting effect on tissue, a substantial coagulation effect on tissue, and an appropriate blend of simultaneous cutting and coagulation effects on tissue. This is accomplished by operating the apparatus at two frequencies within the ultrasonic spectrum, where the first frequency is selected at the low end of the spectrum for enhanced tissue cutting performance, and the second frequency is approximately three times higher for enhanced tissue coagulation performance. The two frequencies may be operated selectively or concurrently, and may be independently adjustable as to amplitude. The ratio 1:3 between the first frequency and the second frequency is an important design consideration that has heretofore not been appreciated in the design of ultrasonic surgical devices. The ratio allows the nodes of the first and second frequencies of the vibrations along the transducer to become aligned, thereby providing appropriate attachment points between the transducer and a casing or handpiece.

In general, the ultrasonic surgical apparatus is comprised of a handpiece, a transducer, a surgical tool, a source of electrical energy, a controller, and a switch. The handpiece has a proximal end to be held and controlled by the surgeon, and a distal end for positioning near the tissue of the patient. The transducer may be composed of magnetostrictive or piezoelectric elements. The transducer is supported within the handpiece and is capable of producing ultrasonic mechanical vibrations selectively or concurrently at a first frequency and at a second frequency, the second frequency approximately three times higher than the first frequency.

While it is understood that a transducer which is operating at a fundamental frequency will also have energy at the higher harmonics, what is described here is the capability of driving the transducer at two frequencies. The surgical tool is supported on the transducer and extends at least partially beyond the distal end of the handpiece. The surgical tool is intended to have a substantial cutting effect on the tissue when the transducer is producing ultrasonic mechanical vibrations at the first (lower) frequency, and the surgical tool is intended to have a substantial coagulation effect on the tissue when the transducer is producing ultrasonic mechanical vibrations at the second (higher) frequency. When the first frequency and the second frequency are operated concurrently, there will result in a substantial combined cutting and coagulation effect on the tissue of the patient.

The source of electrical energy is connected to the transducer. The controller is connected to the source of electrical energy and also connected to the transducer for stably controlling the frequency and amplitude of the ultrasonic mechanical vibrations. To accomplish this, the controller senses frequency and amplitude and then adjusts the source of electrical energy in a way that maintains the desired frequency and amplitude of the transducer.

A switch is connected to the controller for selecting ultrasonic mechanical vibrations at the first frequency, or ultrasonic mechanical vibrations at the second frequency, or ultrasonic mechanical vibrations concurrently at the first frequency and at the second frequency.

In one embodiment, the controller is adjustable by the surgeon. This makes it possible for the surgeon to set the desired amplitude of the mechanical vibrations. To do this, an adjustor is connected to the controller. The adjustor would be capable of independently setting the amplitude of the ultrasonic mechanical vibrations while operating at the first frequency or the second frequency.

Another advantage of having the two frequencies in the ratio 1:3 is that there will be at least one null position along the transducer at which the displacement nodes of vibration for both frequencies will be substantially aligned. There will be little relative motion at the null position between the transducer and the casing of the handpiece. Therefore, it will be possible to attach the transducer to the casing of the handpiece with a support at a null position.

Also claimed is a method for using an ultrasonic surgical apparatus which includes the steps of: developing an ultrasonic resonance at a first frequency; developing an ultrasonic resonance at a second frequency which is approximately three times greater than the first frequency; and resonating an ultrasonic transducer at the first frequency concurrently with the second frequency. There may also be the additional steps of adjusting the amplitude of the first frequency, and adjusting the amplitude of the second frequency.

Also claimed is a method of manufacturing the ultrasonic surgical apparatus where the transducer is mounted within the casing of the handpiece, and the mounting locations are selected at positions along the transducer corresponding to vibration displacement nodes common to both the first frequency and the second frequency.

BRIEF DESCRIPTION OF THE DRAWINGS

FIG. 1 is a schematic block diagram of a Dual Mode Ultrasonic Surgical Apparatus.

FIG. 2 is a schematic block diagram of one embodiment of a handpiece for a Dual Mode Ultrasonic Surgical Apparatus.

FIG. 3 is a schematic block diagram of an alternative embodiment of a handpiece for a Dual Mode Ultrasonic Surgical Apparatus.

DETAILED DESCRIPTION OF THE INVENTION

Figure 4:
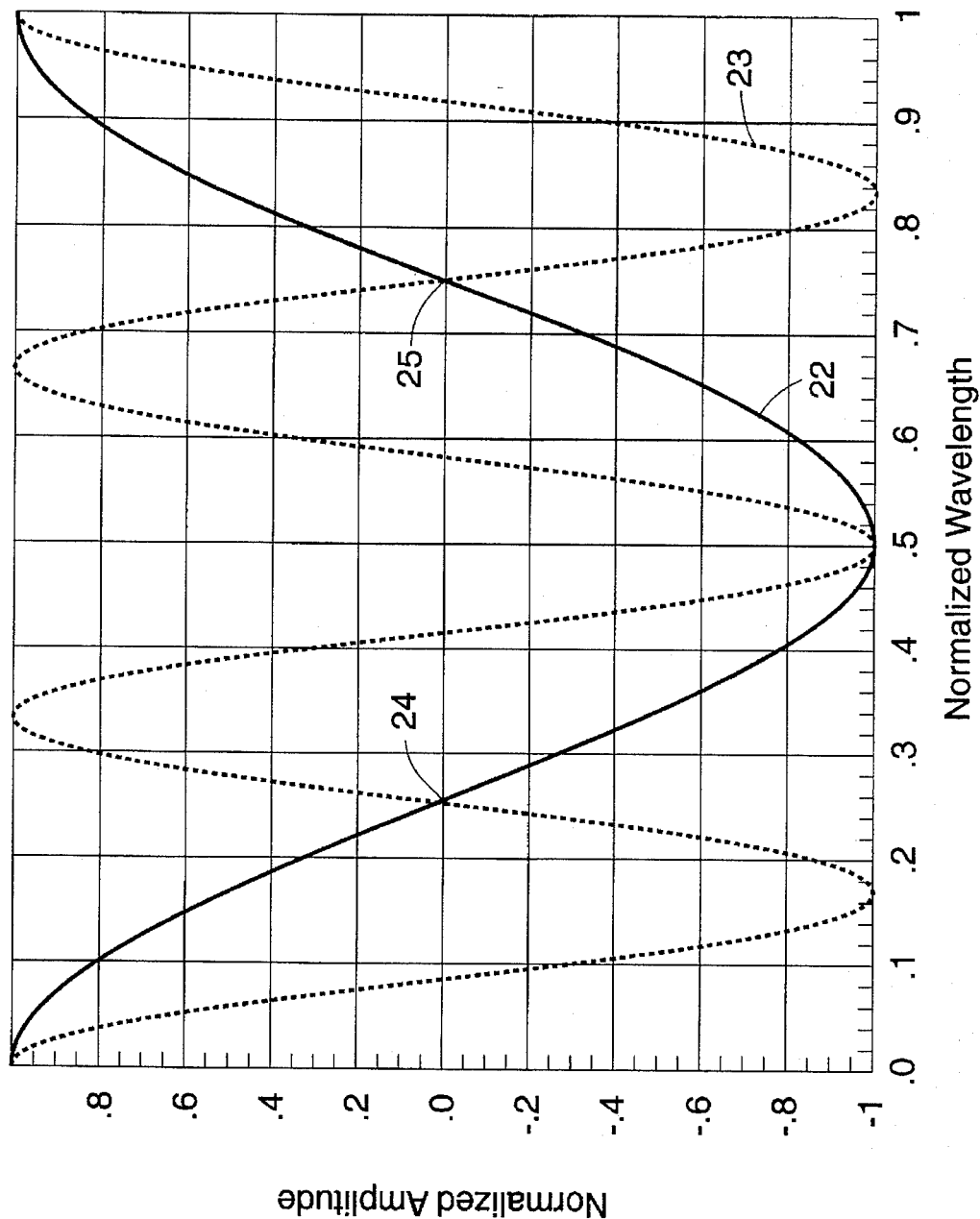
FIG. 4 is a normalized graph depicting the relationship between the first frequency and the second frequency.

A Dual Mode Ultrasonic Surgical Apparatus 10 is shown in FIG. 1. In general, the ultrasonic surgical apparatus is comprised of a handpiece 11, a transducer 14, a surgical tool 16, a source of electrical energy 17, a controller 18, and a switch 19. The Apparatus 10 has a handpiece 11 with a proximal end 12 and a distal end 13. The handpiece 11 has an ultrasonic transducer 14 supported within a casing 15. A surgical tool 16 is supported on the ultrasonic transducer 14.

The handpiece 11 has a proximal end 12 to be held and controlled by the surgeon, and a distal end 13 for positioning near the tissue of the patient. The transducer 14 may be composed of magnetostrictive elements 20 as shown in FIG. 2. Alternatively, the transducer 14 may be composed of piezoelectric elements 21 as shown in FIG. 3.

The transducer 14 is capable of producing ultrasonic mechanical vibrations selectively or concurrently at a first frequency 22 and at a second frequency 23 as shown in FIG. 4. The frequencies 22 and 23 are shown in a normalized fashion in FIG. 4 because the important design consideration is the ratio between the two frequencies 22 and 23. The second frequency 23 is approximately three times higher in frequency than the first frequency 22. The locations of the vibration nodes corresponding to both the first frequency 22 and the second frequency 23 are shown as locations 24 and 25 in FIG. 4.

The surgical tool 16 is supported on the transducer 14 and extends at least partially beyond the distal end of the handpiece 13. The surgical tool 16 is intended to have a substantial cutting effect on the tissue when the transducer 14 is producing ultrasonic mechanical vibrations at the first frequency 22, and the surgical tool 16 is intended to have a substantial coagulation effect on the tissue when the transducer 14 is producing ultrasonic mechanical vibrations at the second frequency 23.

The source of electrical energy 17 is connected to the transducer 14. The design of the source of electrical energy 17 may be realized in many forms which are old and well known in the art. The controller 18 is connected to the source of electrical energy 17 and also connected to the transducer 14 for stably controlling the frequency and amplitude of the ultrasonic mechanical vibrations. To accomplish this, the controller 18 senses frequency and amplitude and then adjusts the source of electrical energy 17 in a way that maintains the desired frequency and amplitude of the transducer 14. The specific design of the controller 18 may be realized in many forms which are old and well known in the art.

A switch 19 is connected to the controller for selecting ultrasonic mechanical vibrations at the first frequency 22, or ultrasonic mechanical vibrations at the second frequency 23, or ultrasonic mechanical vibrations concurrently at the first frequency 22 and at the second frequency 23.

In one embodiment, the controller 18 is adjustable by the surgeon. This makes it possible for the surgeon to set the desired amplitude of the mechanical vibrations. To do this, an adjustor 26 is connected to the controller 18. The adjustor 26 would be capable of independently setting the amplitude of the ultrasonic mechanical vibrations while operating at the first frequency 22 or the second frequency 23.

Another advantage of having the two frequencies in the ratio 1:3 is that there will be at least one position along the transducer 14 at which the nodes of vibration for both frequencies 22 and 23 will be aligned. Therefore, there will be no relative motion of the transducer 14 at that location and it will be possible to attach the transducer 14 to the casing 15. As such, at least one support 27 can be connected between the casing 15 and the transducer 14, and the support 27 may be positioned along the transducer 14 at a location that corresponds to a vibration node common to both the first frequency and the second frequency 24 and 25 as shown in FIG. 4.

Also claimed is a method for using an ultrasonic surgical apparatus 10 which includes the steps of: developing an ultrasonic resonance at a first frequency 22; developing an ultrasonic resonance at a second frequency 23 which is approximately three times higher in frequency than the first frequency 22; and resonating an ultrasonic transducer 14 at the first frequency 22 concurrently with the second frequency 23 wherein the nodes of vibration in the transducer 14 at the first frequency 22 are aligned with the nodes of vibration in the transducer 14 at the second frequency 23 as shown at locations 24 and 25 in FIG. 4.

In one embodiment, there may also be the additional steps of adjusting the amplitude of the first frequency 22, adjusting the amplitude of the second frequency 23, and adjusting the amplitude of the first frequency 22 independently of the second frequency 23. Also claimed is a method of manufacturing a Dual Mode Ultrasonic Surgical Apparatus 10 wherein the transducer 14 is mounted within a handpiece 11 at mounting locations 27 which are at positions selected along the transducer 14 which correspond to vibration nodes common to both the first frequency 22 and the second frequency 23 as shown by positions 24 and 25 in FIG. 4.

What is claimed is:

1. An ultrasonic surgical apparatus used by a surgeon for operating on tissue of a patient, the ultrasonic surgical apparatus including a source of electrical energy, the ultrasonic surgical apparatus comprising:

a handpiece having a easing to be held and controlled by the surgeon;

a distal end on the handpiece for positioning near the tissue of the patient;

a transducer supported within the handpiece, the transducer arranged for producing ultrasonic mechanical vibrations substantially at a first frequency and substantially at a second frequency, the second frequency approximately three times higher in frequency than the first frequency, the vibrations substantially at the first frequency having a first amplitude, the vibrations substantially at the second frequency having a second amplitude;

a controller connected to the source of electrical energy and connected to the transducer, the controller designed to stably control the first amplitude and the second amplitude;

a surgical tool supported on the transducer and extending generally beyond the distal end, the surgical tool having a substantial curing effect on the tissue when operated selectively at the first frequency, the surgical tool having a substantial coagulation effect on the tissue when operated selectively at the second frequency, the surgical tool having substantial curing and coagulating effects on the tissue when operated concurrently at the first and second frequencies.

2. The apparatus of claim 1 wherein an adjuster is connected to the controller, the adjuster able to be used by the surgeon to change the first amplitude and the second amplitude.

3. The apparatus of claim 1 wherein the transducer includes a piezoelectric element.

4. The apparatus of claim 1 wherein the transducer includes a magnetostrictive element.

5. The apparatus of claim 1 wherein at least one support is connected between the handpiece and the transducer, the support positioned along the transducer at a location that substantially corresponds to a vibration displacement node common to both the first frequency and the second frequency.

6. An ultrasonic surgical apparatus used by a surgeon for operating on tissue of a patient comprising:

a handpiece having a proximal end to be held and controlled by the surgeon;

a distal end on the handpiece for positioning near the tissue of the patient;

a transducer supported within the handpiece, the transducer capable of producing ultrasonic mechanical vibrations substantially at a first frequency and substantially at a second frequency, the second frequency approximately three times higher in frequency than the first frequency;

a surgical tool supported on the transducer and extending generally beyond the distal end, the surgical tool having a substantial curing effect on the tissue when operated selectively at the first frequency, the surgical tool having a substantial coagulation effect on the tissue when operated selectively at the second frequency, the surgical tool having substantial curing and coagulating effects on the tissue when operated concurrently at the first and second frequencies;

a source of electrical energy connected to the transducer;

a controller between the source of electrical energy and the transducer for generating signals to stably control the frequencies and amplitudes of the ultrasonic mechanical vibrations of the transducer;

a switch connected to the controller for selecting the signals to stably control the ultrasonic mechanical vibrations of the transducer at the first frequency, or ultrasonic mechanical vibrations of the transducer at the second frequency, or ultrasonic mechanical vibrations of the transducer concurrently at the first frequency and at the second frequency;

an adjuster connected to the controller, the adjuster able to be used by the surgeon to change the signals generated by the controller for setting the amplitude of the ultrasonic mechanical vibrations, and at least one support connected between the handpiece and the transducer, the support positioned along the transducer at a location that substantially corresponds to a vibration displacement node common to both the first frequency and the second frequency.

7. A method for using an ultrasonic surgical apparatus for operating on tissue, the method including the steps of:

developing an ultrasonic resonance substantially at a first frequency which has a first amplitude;

developing an ultrasonic resonance substantially at a second frequency which has a second amplitude, the second frequency approximately three times higher in frequency than the first frequency;

resonating an ultrasonic transducer substantially at the first frequency concurrently with resonating the ultrasonic transducer substantially at the second frequency, stably controlling the first amplitude and the second amplitude with a controller, and applying the ultrasonic surgical apparatus to the tissue for surgical operations.

8. The method of claim 7 with the additional steps of adjusting the first amplitude, and adjusting the second amplitude.

9. A method for manufacturing an ultrasonic surgical handpiece, the handpiece incorporating a casing component to be held by a surgeon and a transducer component to be supported within the casing, the transducer component arranged for producing ultrasonic mechanical vibrations at a first frequency for cutting tissue and at a second frequency for coagulating tissue, the vibrations conducted to a surgical tool on a distal end of the handpiece, the first frequency having a first amplitude and the second frequency having a second amplitude, wherein the second frequency is approximately three times higher in frequency than the first frequency, the method including the steps of:

supporting the transducer within the casing at one or more mounting locations;

positioning the one or more mounting locations along the transducer substantially at vibration displacement nodes common to both the first frequency and the second frequency, and connecting the transducer to a controller capable of controlling the first amplitude and the second amplitude to thereby provide an ultrasonic surgical handpiece for cutting and coagulating tissue.

* * * * *